United States Patent [19]

Dunn et al.

[11] Patent Number: 5,463,029
[45] Date of Patent: Oct. 31, 1995

[54] PURIFICATION OF FUSION PROTEINS COMPRISING GM-CSF AND IL-3

[75] Inventors: Joseph T. Dunn, Woodinville; Stephen M. Waugh, Seattle, both of Wash.

[73] Assignee: Immunex Corporation, Seattle, Wash.

[21] Appl. No.: 979,949

[22] Filed: Nov. 23, 1992

[51] Int. Cl.[6] .............................. C07K 1/18; C07K 19/00; C12N 15/24; C12N 15/27
[52] U.S. Cl. .................. 530/416; 435/69.5; 435/69.52; 435/69.7; 435/254.11; 435/252.3; 435/240.1; 435/320.1; 530/412
[58] Field of Search .......................... 435/69.52, 240.1, 435/320.1, 69.5, 254.11, 252.3, 172.3, 69.7; 530/416, 412

[56] References Cited

U.S. PATENT DOCUMENTS

| 4,658,018 | 4/1987 | Urdal et al. | 530/351 |
| 5,073,627 | 12/1991 | Curtis et al. | 530/351 |
| 5,108,910 | 4/1992 | Curtis et al. | 435/69.7 |
| 5,128,450 | 7/1992 | Urdal et al. | 530/351 |
| 5,204,447 | 4/1993 | Bishop et al. | 530/381 |

FOREIGN PATENT DOCUMENTS

| 0183350 | 1/1992 | European Pat. Off. . |
| 0212914 | 2/1992 | European Pat. Off. . |

OTHER PUBLICATIONS

Werner et al., 1988, Drug Research, 38, 422–428.
Scopes, Protein Purification, 75–101, 1982, Springer–Verlag, New York.

Primary Examiner—Garnette D. Draper
Assistant Examiner—Sally P. Teng
Attorney, Agent, or Firm—Patricia Anne Perkins

[57] ABSTRACT

A process for purifying a fusion protein comprising GM-CSF and IL-3 is disclosed.

20 Claims, No Drawings

PURIFICATION OF FUSION PROTEINS COMPRISING GM-CSF AND IL-3

BACKGROUND OF THE INVENTION

The present invention relates generally to protein chemistry of analogs of granulocyte-macrophage colony stimulating factor (GM-CSF) and Interleukin-3 (IL-3) proteins, fusion proteins comprising GM-CSF and IL-3, and more particularly to a process for purifying such analogs and fusion proteins.

The differentiation and proliferation of hematopoietic cells is regulated by secreted glycoproteins collectively known as colony-stimulating factors (CSFs). In humans, these proteins include granulocyte-macrophage CSF (GM-CSF), which promotes granulocyte and macrophage production from normal bone marrow, and which also appears to regulate the activity of mature, differentiated granulocytes and macrophages. Interleukin-3 (IL-3; also known as multi-CSF) also stimulates formation of a broad range of hematopoietic cells, including granulocytes, macrophages, eosinophils, mast cells, megakaryocytes and erythroid cells. GM-CSF and IL-3 thus have considerable overlap in their broad range of biological activities.

The biological activities of GM-CSF and IL-3 are mediated by binding to specific cell surface receptors expressed on prime cells and in vitro cell lines. Certain of these cell surface receptors bind GM-CSF alone, while others bind IL-3 alone. There also appears to be a class of receptor that binds both IL-3 and GM-CSF (Park et al., J. Biochem. 264:5420, 1989), referred to as GM-CSF/IL-3 receptor.

Fusion proteins comprising GM-CSF and IL-3 and DNA sequences encoding such fusion proteins are described in U.S. Pat. Nos. 5,073,627 and 5,108,910, respectively, both of which are incorporated by reference herein. The fusion proteins are more biologically active than GM-CSF or IL-3 alone or in combination and, relative to IL-3, have a significantly higher affinity of binding to cell lines that express GM-CSF/IL-3 receptors as compared to cell lines with receptors that bind only IL-3 or GM-CSF.

U.S. Pat. Nos. 5,073,627 and 5,108,910 also disclose methods of purifying the fusion proteins. The methods disclosed involve a combination of ion exchange chromatography steps and reverse-phase high-performance liquid chromatography (RP-HPLC). RP-HPLC is difficult to scale-up to a level achieving commercially significant yields of proteins, and additionally requires use of organic solvents. The organic solvents present a number of safety hazards, from the generation of noxious and harmful fumes to risk of explosion. Furthermore, organic solvents require implementation of hazardous waste disposal procedures, and are more likely to result in denaturation or inactivation of biological material than procedures which more nearly mimic physiologic conditions.

Ion exchange chromatography, usually entailing a series of ion exchange steps, may be used to purify proteins. The number and sequence of ion exchange steps, and the optimal purification conditions, are usually determined empirically for individual proteins. The steps and conditions necessary for purification of a fusion protein cannot be predicted by analyzing the physicochemical properties of the proteins from which the fusion protein is derived. As an example of this, the recombinant fusion proteins described herein, which comprise GM-CSF and IL-3, can be adsorbed to an anion exchange resin such as a resin having pendant diethylaminoethyl (DEAE) groups, and eluted at a fairly acidic pH, whereas IL-3 would not be adsorbed to an anion exchange resin having pendant DEAE groups under these conditions.

Therefore, there is a need in the art to develop methods of purifying fusion proteins comprising GM-CSF and IL-3 that circumvent the use of RP-HPLC and are amenable to scaleup to the level required for commercial success.

SUMMARY OF THE INVENTION

The present invention provides a process for purifying a recombinant fusion protein comprising GM-CSF and IL-3 from an aqueous solution, comprising adsorbing the recombinant fusion protein to a cation exchange resin, eluting the recombinant fusion protein from the cation exchange resin; adsorbing the recombinant fusion protein eluted from the cation exchange resin to a first anion exchange resin, eluting the recombinant fusion protein from the first anion exchange resin; adsorbing the recombinant fusion protein eluted from the first anion exchange resin to a second anion exchange resin and eluting the recombinant fusion protein from the second anion exchange resin. The recombinant fusion protein eluted from the second anion exchange step may be adsorbed to a second cation exchange resin, and eluted.

DETAILED DESCRIPTION OF THE INVENTION

The process of the present invention involves purifying recombinant fusion proteins comprising GM-CSF and IL-3 from fluid containing the recombinant fusion proteins by a series of ion exchange chromatography steps. The ion-exchange steps circumvent the need to use reverse phase high-performance liquid chromatography (RP-HPLC), thus removing the risks associated with the use of organic solvents that RP-HPLC requires. By avoiding the use of organic solvents, the process is ideally suited for scale-up to provide commercial quantities of recombinant fusion proteins comprising GM-CSF and IL-3.

As used herein, the term "GM-CSF" refers to proteins having amino acid sequences which are substantially similar to the native human granulocyte-macrophage colony-stimulating factor amino acid sequences (e.g., ATCC 53157) and which are biologically active in that they are capable of binding to GM-CSF receptors, transducing a biological signal initiated by binding GM-CSF receptors, or cross-reacting with antibodies raised against GM-CSF. Such sequences are disclosed, for example, in Anderson et al. (Proc. Nat'l. Acad. Sci. USA 82:6250, 1985). The term "GM-CSF" also includes analogs of GM-CSF molecules which exhibit at least some biological activity in common with native human GM-CSF. Exemplary analogs of GM-CSF are disclosed in EP Publ. No. 212914 (U.S. Ser. No. 06/763,130), which describes GM-CSF analogs having KEX2 protease cleavage sites inactivated so as to increase expression of GM-CSF in yeast hosts, and in WO Publ. No. 89/03881 (U.S. Pat. No. 5,032,676), which describes GM-CSF analogs having various glycosylation sites eliminated.

The term "IL-3" refers to proteins having amino acid sequences which are substantially similar to the native human Interleukin-3 amino acid sequences and which are biologically active in that they are capable of binding to IL-3 receptors or transducing a biological signal initiated by binding to IL-3 receptors, or cross-reacting with anti-IL-3 antibodies raised against IL-3. Such sequences are disclosed, for example, in EP Publ. Nos. 275,598 and 282,185. The term "IL-3" also includes analogs of IL-3 molecules which exhibit at least some biological activity in common with native IL-3. Exemplary analogs of IL-3 are also disclosed in U.S. Pat. No. 5,128,450.

As used herein, the term "fusion protein" refers to C-terminal to N-terminal fusions of GM-CSF and IL-3. Exemplary fusion proteins are disclosed in U.S. Pat. Nos. 5,073,627 and 5,108,910, which are incorporated by reference herein. The fusion proteins of the present invention include constructs in which the C-terminal portion of GM-CSF is fused to the N-terminal portion of IL-3, and also constructs in which the C-terminal portion of IL-3 is fused to the N-terminal portion of GM-CSF. Specifically, the fusion proteins of the present invention have a formula selected from the group consisting of $$R_1-R_2, R_2-R_1, R_1-L-R_2 \text{ and } R_2-L-R_1$$

wherein $R_1$ is GM-CSF; $R_2$ is IL-3; and L is a linker peptide sequence. GM-CSF is linked to IL-3 in such a manner as to produce a single protein which retains the biological activity of GM-CSF and IL-3. Specific fusion protein constructs are named by listing the GM-CSF and IL-3 domains in the fusion protein in their order of occurrence (with the N terminal domain specified first, followed by the C-terminal domain). Thus, GM-CSF/IL-3 refers to a fusion protein comprising GM-CSF followed by IL-3 (i.e., the C-terminus of GM-CSF is linked to the N-terminus of IL-3), and huGM-CSF[Leu$^{23}$Asp$^{27}$Glu$^{39}$]/huIL-3[Pro$^8$Asp$^{15}$Asp$^{70}$] refers to a fusion protein in which the N-terminal region of the fusion construct is huGM-CSF[Leu$^{23}$Asp$^{27}$Glu$^{39}$], and the C-terminal region is huIL 3[Pro$^8$Asp$^{15}$Asp$^{70}$]. Unless otherwise specified, the terms GM-CSF/IL-3 and IL-3/GM-CSF refer to fusion proteins with a linker sequence added.

Source of Recombinant Fusion Proteins comprising GM-CSF and IL-3

Exemplary methods for producing fusion proteins comprising GM-CSF and IL-3 are described in U.S. Pat. Nos. 5,073,627 and 5,108,910, which have been incorporated by reference herein. Briefly, a DNA sequence encoding a fusion protein is constructed using recombinant DNA techniques to assemble separate DNA fragments encoding GM-CSF and IL-3 into an appropriate expression vector. The 3' end of a DNA fragment encoding GM-CSF is ligated to the 5' end of the DNA fragment encoding IL-3, with the reading frames of the sequences in phase to permit mRNA translation of the sequences into a single biologically active fusion protein. The resulting protein is, for example, huGM-CSF[Leu$^{23}$Asp$^{27}$Glu$^{39}$]/huIL-3[Pro$^8$Asp$^{15}$Asp$^{70}$]. Alternatively, the 3' end of a DNA fragment encoding IL-3 may be ligated to the 5' end of the DNA fragment encoding GM-CSF, with the reading frames of the sequences in phase to permit mRNA translation of the sequences into a single biologically active fusion protein, yielding the protein huIL-3 [Pro$^8$Asp$^{15}$Asp$^{70}$]/huGM-CS F[Leu$^{23}$Asp$^{27}$Glu$^{39}$].

The DNA fragments are operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation. The ability to replicate in a host, usually conferred by an origin of replication, and a selection gene to facilitate recognition of transformants may additionally be incorporated. The regulatory elements responsible for transcription of DNA into mRNA are retained on the first of the two DNA sequences, while binding signals or stop codons, which would prevent read-through to the second DNA sequence, are eliminated. Conversely, regulatory elements are removed from the second DNA sequence while stop codons required to end translation are retained.

A linker sequence may be incorporated into the fusion protein construct by well known standard methods of mutagenesis. The linker sequence is used to separate GM-CSF and IL-3 domains by a distance sufficient to ensure that each domain properly folds into its secondary and tertiary structures. Suitable linker sequences (1) will adopt a flexible extended conformation, (2) will not exhibit a propensity for developing an ordered secondary structure which could interact with the functional GM-CSF and IL-3 domains, and (3) will have minimal hydrophobic or charged character which could promote interaction with the functional protein domains. Typical surface amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, may also be used in the linker sequence. Amino acid sequences useful as linkers of GM-CSF and IL-3 include, by way of example, a series of four Gly residues followed by a Ser residue, four Gly residues, another Ser residue, four more Gly residues and a final Ser residue, and, as another example, four Gly residues followed by a Ser residue, five additional Gly residues and a final Ser residue.

The length of the linker sequence may vary without significantly affecting the biological activity of the fusion protein. Linker sequences are unnecessary where the proteins being fused have non-essential N- or C-terminal amino acid regions which can be used to separate the functional domains and prevent steric interference. In one preferred embodiment of the present invention, the C-terminus of GM-CSF may be directly fused to the N-terminus of IL-3. In another preferred aspect of the invention, a linker sequence length of about 11 amino acids is used to provide a suitable separation of functional protein domains, although longer linker sequences may also be used. The linker sequence may be from 1 to 500 amino acids in length, or more preferably from 1 to 100 amino acids in length. In the most preferred aspects of the present invention, the linker sequence is from about 1–20 amino acids in length. In the specific embodiments disclosed herein, the linker sequence is from about 5 to about 15 amino acids, and is advantageously from about 10 to about 15 amino acids.

In a most preferred embodiment of the invention, cDNA encoding human IL-3 was isolated from a library prepared from poly A$^+$RNA from isolated peripheral blood lymphocytes. Recombinants were screened by standard plaque hybridization techniques using two oligonucleotide probes with sequences complementary to selected 5' and 3' sequences of the huIL-3 gene. DNA was isolated from those clones which hybridized to the probes, and analyzed by additional hybridization experiments. After isolating a single clone that hybridized to each of the probes, the hybridizing cDNA bearing the IL-3 gene was subcloned and sequenced by conventional techniques. The cDNA encoded a proline residue at position 8 of the mature protein. Two asparagine-linked glycosylation sites present in native IL-3 (Asn$^{15}$ and Asn$^{70}$) were altered by changing the codons at these positions to ones that encode aspartic acid, to prevent N-linked glycosylation (often hyperglycosylation) of the secreted protein by the yeast cells. In vitro mutagenesis was conducted by a method similar to that described by Walder and Walder, Gene 42:133 (1986). The final yeast vector was designated pIXY151. This vector, when present in yeast, allows glucose-regulated expression and secretion of rhuIL-3 (Pro$^8$Asp$^{15}$Asp$^{70}$).

The wild-type gene coding for human GM-CSF, resident on plasmid pHG23, has been deposited with the American Type Culture Collection (ATCC), 12301 Parklawn Drive, Rockville, Md. 20852, USA, under accession number 39900. The wild-type gene inserted in a yeast expression vector, pYαfHuGM, has also been deposited with the ATCC under accession number 53 157. In order to provide a non-glycosylated analog of human GM-CSF, oligonucleotide-directed site-specific mutagenesis procedures were employed to eliminate potential N-glycosylation sites, as described in PCT publication WO 89/03881. A plasmid encoding this analog, huGM-CSF (Leu$^{23}$Asp$^{27}$Glu$^{39}$), was deposited with the ATCC as plasmid L207-3 in E. coli strain RR1 under accession number 67231.

In order to create a secretion vector for expressing a fusion construct having human GM-CSF and human IL-3 separated by a linker sequence, a precursor plasmid was first constructed by directly fusing DNAs encoding GM-CSF and IL-3 together without regard to reading frame or intervening sequences. A cDNA fragment encoding nonglycosylated human GM-CSF was excised from plasmid L207-3 as a 977bp restriction fragment (Sph1 to Ssp1). An IL-3 cDNA was excised from pIXY151 by digestion with Asp718, which was then blunt-ended using the T4 polymerase reaction of Maniatas et al. (Molecular Cloning: A Laboratory Manual, Cold Spring Harbor, 1982, p. 118) and further digested with Xho1 giving an 803 bp fragment. These two fragments were then directly ligated; this plasmid was called GM/IL-3 direct fusion.

The GM/IL-3 direct fusion plasmid was used as a template in oligonucleotide-directed mutagenesis using methods similar to those described by Walder and Walder, supra. An oligonucleotide that overlapped the 3' end of GM-CSF by 13 bp (without the stop codon), contained the Gly Ser linker, and overlapped the 5' end of IL-3 by 13 bp was synthesized. Oligonucleotide directed mutagenesis was carried out by annealing the oligonucleotide to single stranded plasmid DNA and transforming yeast strain XV2181 with annealed DNA as described by Walder and Walder, supra. Yeast transformants were selected by growth on medium lacking tryptophan, pooled, and DNA was extracted as described by Holm et al. (Gene42:169, 1986). This DNA, containing a mixture of mutant and wild type plasmid DNA, was used to transform E. coli RR1 to ampicillin resistance. The resulting colonies were screened by hybridization to radiolabeled oligonucleotide using standard techniques. Plasmids comprising DNA encoding GM-CSF/linker/IL-3 were identified by their hybridization to radiolabeled oligonucleotide containing the linker under stringent conditions and verified by nucleotide sequencing.

During nucleotide sequencing it was discovered that a mutation had occurred within the linker region which resulted in the expression of a protein in which the sequence of amino acids GlyGlySerGly were deleted. This mutation did not change the reading frame or prevent expression of a biologically active protein. The resulting plasmid was designated pIXY321 and expressed the fusion protein huGM-CSF[Leu$^{23}$Asp$^{27}$Glu$^{39}$]/Gly$_4$SerGly$_5$Ser/huIL-3 [Pro$^8$Asp$^{15}$Asp$^{70}$].

In another embodiment of the invention, a plasmid encoding a fusion protein comprising an N-terminal IL-3 and a C-terminal GM-CSF was constructed in a similar manner to that described for pIXY321. The plasmid, designated pIXY344, expressed the fusion protein huIL-3 [Pro$^8$Asp$^{15}$Asp$^{70}$]/(Gly$_4$Ser)$_3$/huGM-CSF[Leu$^{23}$Asp$^{27}$Glu$^{39}$].

Protein Expression in Recombinant Microbial Systems

Transformed host cells are cells which have been transformed or transfected with fusion protein expression vectors constructed using recombinant DNA techniques. Purified mammalian fusion proteins or analogs are prepared by culturing suitable transformed host cells to express the recombinant translation products of the DNAs of the present invention, which are then purified from culture media or cell extracts. Suitable host cells for expression of fusion protein include prokaryotes, yeast or higher eukaryotic cells under the control of appropriate promoters. Cell-free translation systems could also be employed to produce fusion protein using RNAs derived from the DNA constructs of the present invention. Appropriate cloning and expression vectors for use with bacterial, fungal, yeast, and mammalian cellular hosts are described by Pouwels et al. (Cloning Vectors: A Laboratory Manual, Elsevier, New York, 1985), the relevant disclosure of which is hereby incorporated by reference.

Recombinant protein produced in bacterial culture is usually isolated by initial extraction from cell pellets, followed by one or more concentration, salting-out, aqueous ion exchange or size exclusion chromatography steps. Microbial cells employed in expression of recombinant fusion proteins can be disrupted by any convenient method, including freeze-thaw cycling, sonication, mechanical disruption, or use of cell lysing agents. The recombinant fusion proteins are further purified as described herein.

In a most preferred embodiment, fermentation of yeast which express fusion proteins as a secreted protein greatly simplifies purification. For example, supernatants from systems which secrete recombinant protein into aqueous culture media can be first concentrated using a commercially available protein concentration filter, for example, an Amicon Spiral Ultrafiltration cartridge or Millipore Pellicon ultrafiltration unit. Following the concentration step, the recombinant fusion proteins are further purified as described herein.

Preferable yeast hosts for expression of recombinant fusion proteins include Saccharomyces species, such as S. cerevisiae. Yeast of other genera such as Pichia, Schizosaccharomyces or Kluyveromyces may also be employed. A particularly preferred yeast host strain is XV2181, a diploid S. cerevisiae strain formed by mating XV617-1-3B [a, his6, leu2-1, trp-1, ura 3, ste5], obtained from the University of Washington, Department of Genetics Yeast Strain Bank, Seattle, WA, USA, and X2181-1B [a, trp-1, gal1, ade1, his2], obtained from the Yeast Genetic Stock Center, University of California, Berkeley, Calif., USA. XV2181 is autotrophic for tryptophan, and prototrophic for uracil and histidine, and can be grown in selective medium to express and secrete recombinant fusion proteins. The types and quantities of the various nutrients in the selective medium may be altered to assure optimal protein expression. The host strain is transformed with expression plasmid by the method of Sherman et al., Laboratory Course Manual for Methods in Yeast Genetics, Cold Spring Harbor Laboratory, 1986.

Yeast vectors will generally contain an origin of replication from the 2μ yeast plasmid or an autonomously replicating sequence (ARS), promoter, DNA encoding the fusion protein, sequences for polyadenylation and transcription termination and a selection gene. Preferably, yeast vectors will include an origin of replication and selectable marker permitting transformation of both yeast and E. coli, e.g., the ampicillin resistance gene of E. coli and S. cerevisiae trp 1 gene, which provides a selection marker for a mutant strain of yeast lacking the ability to grow in tryptophan, and a promoter derived from a highly expressed yeast gene to induce transcription of a structural sequence downstream.

The presence of the trp1 lesion in the yeast host cell genome then provides an effective environment for detecting transformation by growth in the absence of tryptophan. Alternatively, transcriptional units and a selectable marker can be stably integrated in the yeast chromosome at a single or multiple sites, and/or with multiple copies per location.

Suitable promoter sequences in yeast vectors include the promoters for metallothionein, 3-phosphoglycerate kinase (Hitzeman et al., J. Biol. Chem. 255:2073, 1980) or other glycolytic enzymes (Hess et al., J. Adv. Enzyme Reg. 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pBR322 for selection and replication in E. coil (Amp$^r$ gene and origin of replication) and yeast DNA sequences including a glucose-repressible ADH2 promoter and $\alpha$-factor secretion leader. The ADH2 promoter has been described by Russell et al. (J. Biol. Chem. 258:2674, 1982) and Beier et al. (Nature 300:724, 1982). The yeast $\alpha$-factor leader, which directs secretion of heterologous proteins, can be inserted between the promoter and the structural gene to be expressed. See, e.g., Kurjan et al., Cell 30:933, 1982; and Bitter et al., Proc. Natl. Acad. Sci. USA 81:5330, 1984. The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., Proc. Natl. Acad. Sci. USA 75: 1929, 1978, selecting for Trp$^+$ transformants in a selective medium consisting of 0.67% yeast nitrogen base, 0.5% casamino acids, 2% glucose, 10 µg/ml adenine and 20 µg/ml uracil.

Host strains transformed by vectors comprising the ADH2 promoter may be grown for expression in a rich medium consisting of 1% yeast extract, 2% peptone, and 1% glucose supplemented with 80 µg/ml adenine and 80 µg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, Bio/Technology 6:47 (1988). Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), HeLa and BHK cell lines. Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., Nature 273:113, 1978). Smaller or larger SV40 fragments may also be used, provided the approximately 250 bp sequence extending from the Hind III site toward the BglI site located in the viral origin of replication is included. Exemplary vectors can be constructed as disclosed by Okayama and Berg (Mol. Cell. Biol. 3:280, 1983).

A useful system for stable high level expression of mammalian receptor cDNAs in C127 murine mammary epithelial cells can be constructed substantially as described by Cosman et al. (Mol. Immunol. 23:935, 1986).

Particularly preferred eukaryotic vectors for expression of GM-CSF/IL-3 DNA include pIXY321 and pIXY344, both of which are yeast expression vectors derived from pBC102.K22 (ATCC 67,255) and contain DNA sequences from pBR322 for selection and replication in E. coli (Amp$^r$ gene and origin of replication) and yeast, as described U.S. Pat. Nos. 5,073,627 and 5,108,910.

Fusion proteins synthesized in recombinant culture are characterized by the presence of non-human cell components, including proteins, in amounts and of a character which depend upon the purification steps taken to recover the fusion protein from the culture. These components ordinarily will be of yeast, prokaryotic or non-human higher eukaryotic origin and preferably are present in innocuous contaminant quantities, on the order of less than about 5 percent by scanning densitometry or chromatography. Further, recombinant cell culture enables the production of the fusion protein free of proteins which may be normally associated with GM-CSF or IL-3 as they are found in nature in their respective species of origin, e.g., in cells, cell exudates or body fluids.

Purification of Recombinant Fusion Proteins

Recombinant fusion proteins comprising GM-CSF and IL-3 may be prepared by culturing transformed host cells under culture conditions necessary to express a recombinant fusion protein. The resulting expressed fusion protein may then be purified from supernatant fluid or fluid prepared from a cell extract. In a most preferred embodiment of the invention, the recombinant fusion protein is purified from the supernatant fluid (fermentation broth) of transformed yeast cells that express the recombinant fusion protein as a secreted protein. Fluid (supernatant or cell extract) containing the recombinant fusion protein is clarified by filtration. Preferably, the pH of the fluid is increased by adding base prior to filtration; more preferably, the pH is adjusted to between 8 and 9. Most preferably, 50% NaOH is added to the fermentation broth to increase the pH to 8.5, and the resulting fluid is clarified by tangential flow filtration through a 0.1–1.0 µm filter (for example, Millipore ProStak filter system). Alternatively, other cell separation techniques may be employed to clarify the fluid. The clarified fluid containing the recombinant fusion protein is concentrated up to about twenty-fold, to produce a convenient volume for further processing, by using a commercially available protein concentration filter, for example, an Amicon Spiral Ultrafiltration cartridge or Millipore Pellicon ultrafiltration unit. The Concentrated fluid is then diafiltered with water to reduce the ionic strength of the fluid. Most preferably, the ionic strength of the diafiltered fluid is less than about 10 mS.

Following the concentration step, the pH of the fluid containing the recombinant fusion protein is reduced, and the fluid is applied to a cation exchange resin. The recombinant fusion protein will adsorb to the cation exchange resin, and can be eluted in a more purified form at acidic pH. Subsequently, the eluted recombinant fusion protein is applied to an anion exchange resin. The recombinant fusion protein will adsorb to the anion exchange resin, and can be eluted in a yet more purified form at a slightly acidic pH. Alternatively, the cation and anion exchange chromatography steps may be performed in the reverse order, in which case the pH of the concentrated fluid is not reduced prior to addition to the anion exchange resin. The progress of the cation and anion exchange steps (and all subsequent chromatography steps) is followed by monitoring absorbance of the fluid being washed or eluted from the column at a wavelength of 280 nm.

Immediately before being applied to a cation exchange resin, the pH of the fluid is adjusted to a pH between 3 and 5, preferably between 4.5 and 5.0. Most preferably, a pH of 4.7 is achieved by the addition of glacial acetic acid. Suitable cation exchange resins include various insoluble matrices comprising sulfonate, sulfopropyl or carboxymethyl groups; sulfopropyl groups are preferred. The matrices can be acrylamide, agarose, dextran, cellulose, silica or other types commonly employed in protein purification. A particularly useful material for cation exchange chromatography of recombinant fusion proteins comprising GM-CSF and IL-3 is SP-Toyopearl™ (Tosoh Corporation, Japan; distributed by Bioseparations Specialists, Philadelphia, Pa.), of which approximately 1.7 L is used per 100 L of fermentation broth. A column of suitable size is prepared with the cation exchange resin, and equilibrated with an appropriate buffer to charge the cation exchange groups. Binding and elution conditions may be optimized for the various suitable ion exchange resins employed. For SP-Toyopearl™, an appropriate buffer will have a $pK_a$ in the range of about 3 to about 5. Preferably, the column is equilibrated with 25 mM sodium acetate buffer, pH 3.8 to 4.2 (equilibration buffer). More preferably, the column is first washed with 250 mM sodium acetate buffer, then washed with equilibration buffer to reduce the ionic strength. Most preferably, the difference in the ionic strength of the equilibration buffer and the effluent is less than about 0.2 mS, and the pH of both is 4.0. When sulfopropyl groups are employed, concentrated fluid containing the recombinant fusion protein is adjusted to a pH of about 4.5, with a suitable acid such as acetic acid. More preferably, the pH of the concentrated fluid is from 4.3 to 4.7. Most preferably, the pH of concentrated fluid is 4.5. The adjusted fluid is then applied to the equilibrated sulfopropyl column. Contaminating proteins are removed by washing the column until the absorbance returns to baseline, with a suitable buffer such as sodium acetate. More preferably, the pH of the buffer is from about 5.3 to about 5.7. Most preferably, the buffer is 25 mM sodium acetate buffer, pH 5.5. The recombinant fusion protein adsorbs to the cation exchange resin, and can be eluted in a more highly purified form by application of a buffer containing salt. Preferably, the buffer is sodium acetate, and the salt is sodium chloride. More preferably, the pH of the buffer is from about 5.3 to about 5.7. The most preferable buffer is 25 mM sodium acetate buffer, pH 5.5, 400 mM sodium chloride. A single elution pool is collected, beginning when the absorbance is seen to rise and continuing beyond the peak until absorbance returns to less than 10% of the full peak height. The eluate is most preferably stored at 2–8° C. Alternatively, the eluate may be stored frozen at less than about −20° C., and thawed prior to the next purification step. The presence of the recombinant fusion protein is determined by sodium dodecyl sulfate polyacrylamide gel electrophoresis (SDS-PAGE) or other suitable means, and the protein concentration is determined using a suitable protein assay. The recombinant fusion protein may also be quantitated by an appropriate functional assay, such as an enzyme-linked immunosorbent assay (ELISA).

Suitable anion exchange resins include various insoluble matrices comprising pendant diethylaminoethyl (DEAE), quaternary amino (QAE) groups, or polyethyleneimine (PEI) groups; DEAE groups are preferred. The matrices can be acrylamide, agarose, dextran, cellulose, silica or other types commonly employed in protein purification. A particularly useful material for anion exchange chromatography of recombinant fusion proteins comprising GM-CSF and IL-3 is DEAE Sepaharose® Fast Flow (Pharmacia, Uppsala, Sweden), of which from about 1.2 to about 2.9 L is used per 100 L of fermentation broth; preferably, the amount is about 2.9 L per 100 L of fermentation broth. A column of suitable size is prepared with the anion exchange resin, and equilibrated with an appropriate buffer to charge the anion exchange groups. Binding and elution conditions may be optimized for the various suitable ion exchange resins employed. For DEAE Sepaharose® Fast Flow, an appropriate buffer will have a $pK_a$ in the range of about 7 to about 9. Preferably, the column is equilibrated with 25 mM TrisHCl buffer, pH 7.8 to 8.2. More preferably, the column is first washed with 500 mM TrisHCl buffer, then washed with 25 mM TrisHCl buffer to decrease the ionic strength. Most preferably, the difference in the ionic strength of the wash buffer and the effluent is less than about 0.2 mS, and the pH of both is 8.0. When DEAE groups are employed, the fluid containing the recombinant fusion protein is diluted with water to decrease the ionic strength, and the pH is increased by the addition of base. Preferably, the conductivity is adjusted to less than about 9 mS, and the pH to greater than about 7. More preferably, sufficient 0.5 M Tris HCl is added to make the fluid 10 mM TrisHCl, and the pH is adjusted to from about 7.8 to about 8.2 with 1 M NaOH. Most preferably, the pH is 8.0. The diluted, adjusted fluid is then applied to the equilibrated DEAE column. Contaminating proteins are removed by washing the column with a suitable buffer such as sodium acetate. More preferably, the pH of the buffer is from about 4.8 to about 5.2. Most preferably, the buffer is 50 mM sodium acetate buffer, pH 5.0. The recombinant fusion protein adsorbs to the anion exchange resin, and can be eluted in a more highly purified form by reducing the pH slightly by the addition of a suitable buffer such as sodium acetate. More preferably, the pH of the buffer is from about 4.3 to about 4.7. Most preferably, the buffer is 50 mM sodium acetate buffer, pH 4.5. A single elution pool is collected, beginning when the absorbance is seen to rise and continuing beyond the peak until absorbance returns to less than 10% of the full peak height. The eluate is most preferably stored at 2–8° C. Alternatively, the eluate may be stored frozen at less than about −20° C., and thawed prior to the next purification step. The presence of the recombinant fusion protein is determined by SDS-PAGE or other suitable means, and the protein concentration is determined using a suitable protein assay. The recombinant fusion protein may also be quantitated by an appropriate functional assay, such as an ELISA.

Following the second ion exchange step, the fluid containing the recombinant fusion protein is applied to a second anion exchange resin. Suitable anion exchange resins include various insoluble matrices comprising DEAE or QAE groups, or weak anion exchange groups such as PEI; PEI groups are preferred. The matrices can be acrylamide, agarose, dextran, cellulose, silica or other types commonly employed in protein purification. A particularly useful material for anion exchange chromatography of recombinant fusion proteins comprising GM-CSF and IL-3 is Bakerbond Wide-pore™ PEI-silica (J. T. Baker, Phillipsburg, N.J.), of which approximately 0.9 L is used per 100 L of fermentation broth. A column of suitable size is prepared with the anion exchange resin, and equilibrated with an appropriate buffer to charge the anion exchange groups. Binding and elution conditions may be optimized for the various suitable ion exchange resins employed. For Bakerbond Wide-pore™ PEI-silica, an appropriate buffer will have a $pK_a$ in the range of about 6 to about 7. Preferably, the column is equilibrated with sodium phosphate buffer, pH 6.3 to 6.7. More preferably, the column is first washed with 500 mM sodium phosphate buffer, then with 10 mM sodium phosphate buffer to reduce the ionic strength. Most preferably, the difference in the ionic strength of the wash buffer and the effluent is less than about 0.2 mS, and the pH of both is 6.5. When PEI groups are employed, the fluid containing the recombinant fusion protein is made 10 mM sodium phosphate, and the pH is adjusted with base. More preferably, the pH is from about 6.3 to about 6.7. Most preferably, the pH is adjusted to 6.5 with 50% NaOH. The pH-adjusted fluid containing the recombinant fusion protein is then applied to the equilibrated PEI column. Contaminating proteins are removed by washing the column with a suitable buffer such as sodium phosphate. More preferably, the pH of the buffer is from about 6.3 to about 6.7. Most preferably, the buffer is 10 mM sodium phosphate buffer, pH 6.5. The recombinant fusion protein is adsorbed to the anion exchange resin, and can be eluted in a more highly purified form by application of a sodium phosphate buffer containing salt. More preferably, the pH of the buffer is from about 6.3 to about 6.7, and the salt is sodium chloride. Most preferably, the buffer is 25 mM sodium phosphate pH 6.5, 400 mM sodium chloride. A single elution pool is collected, beginning when the absorbance is seen to rise and continuing beyond the peak until absorbance returns to less than 10% of the full peak height. The eluate is most preferably stored at 2–8° C. Alternatively, the eluate may be stored frozen at less than about −20° C., and thawed prior to the next purification step. The presence of the recombinant fusion protein is determined by SDS-PAGE or other suitable means, and the protein concentration is determined using a suitable protein assay. The recombinant fusion protein may also be quantitated by an appropriate functional assay, such as an ELISA.

A second cation exchange resin can be employed to further purify the recombinant fusion protein. Suitable cation resins include various insoluble matrices comprising sulfonate, sulfopropyl or carboxymethyl groups; sulfopropyl groups are preferred. The matrices can be acrylamide, agarose, dextran, cellulose, silica or other types commonly employed in protein purification. A particularly useful material for cation exchange chromatography of recombinant fusion proteins comprising GM-CSF and IL-3 is Fractogel® SO3-650 (E. Merck, Darmstadt, Germany; distributed by EM Separation, Gibbstown, N.J.), of which approximately 1.25 L is used per 100 L of fermentation broth. A column of suitable size is prepared with the cation exchange resin, and equilibrated with an appropriate buffer to charge the cation exchange groups. Binding and elution conditions may be optimized for the various suitable ion exchange resins employed. For Fractogel® $SO_3$-650, an appropriate buffer will have a $pK_a$ in the range of from about 3 to about 5. Preferably, the column is equilibrated with sodium acetate, pH 3.8 to 4.2. More preferably, the column is first washed with 250 mM sodium acetate buffer, then washed with 25 mM sodium acetate buffer to decrease the ionic strength. Most preferably, the difference in the ionic strength of the wash buffer and the effluent is less than about 0.2 mS, and the pH of both is 4.0. When sulfopropyl groups are employed, the fluid containing recombinant fusion protein is diluted with water to reduce the ionic strength of the fluid, and the pH is reduced. Preferably, the ionic strength of the fluid is less than about 10 mS, and the pH is from about 3.8 to about 4.2. Most preferably, the fluid is made 10 mM with sedium acetate and the pH adjusted with acetic acid to 4.0. The adjusted fluid is then applied to the equilibrated sulfopropyl column. Contaminating proteins are removed by washing the column with sodium acetate buffer. Preferably the pH of the sodium acetate buffer is from about 3 to about 5. More preferably, the pH of the sodium acetate buffer is from about 3.8 to about 4.2. Most preferably, the sodium acetate buffer is 25 mM sodium acetate, pH 4.0. The column is then washed with a second wash buffer having a slightly higher pH. Preferably, the pH of the second wash buffer is from about 5 to about 6. More preferably, the buffer is 4-morpholineethanesulfonic acid (MES) buffer. Most preferably, the buffer is 25 mM MES, pH 5.5 (Buffer A). The recombinant fusion protein is adsorbed to the cation exchange resin, and can be eluted with a linear salt gradient. Preferably, the linear salt gradient is established in 25 mM MES buffer. More preferably, the pH of the linear salt gradient is from about 5.3 to about 6.2. Most preferably, a 15-column volume linear gradient of 25 mM MES, pH 6.0, 0.5 M NaCl (Buffer B) is established from 100% Buffer A to 100% Buffer B. Fractions of approximately 20% of the column volume are collected; those fractions containing the purified fusion protein are identified by SDS-PAGE or other suitable means, and pooled. Alternatively, a single elution pool is collected, beginning when the absorbance is seen to rise and continuing beyond the peak until absorbance returns to less than 10% of the full peak height. The fractions, or the pool, are most preferably stored at 2–8° C. Alternatively, the fractions or the pool may be stored frozen at less than about −20° C, and thawed prior to the next procedure. The protein concentration is determined using a suitable protein assay. The recombinant fusion protein may also be quantitated by an appropriate functional assay, such as an ELISA.

Some or all of the foregoing purification steps, in various combinations, can also be employed to provide a homogeneous recombinant fusion protein. Additional steps may also be employed to optimize preparation of recombinant fusion protein preparations. Filtration steps may be included to ensure the sterility of the recombinant fusion proteins. Such filtration steps would include filtering the fluid containing the recombinant fusion proteins with an absolute 0.2 μm filter such as a Millipore Millipak 20 into a sterile container. The purified protein may be concentrated to provide a convenient volume for storage or preparation of a composition for injection, and exchanged into an appropriate buffer. Concentration to at least about 5 mg/ml purified recombinant fusion protein is preferred. A preferred buffer is 0.1 M Tris, pH 7.4. For example, the purified protein may be concentrated by ultrafiltration, then diafiltered against at least five volumes of 0.1 M Tris, pH 7.4 to yield a solution of at least 5 mg/ml recombinant fusion protein, with pH from about 7.2 to about 7.6. Alternatively, an additional cation exchange step may be performed to concentrate the recombinant fusion protein and exchange the buffer. For example, the pH of the purified protein is adjusted to 4.0, and the purified protein is applied to another cation exchange resin to a very high protein concentration. A preferred cation exchange resin is Fractogel® SO$_3$-650. The purified protein is then eluted from the cation exchange resin with 0.1 M Tris, pH 7.4, to yield a solution of at least 5 mg/ml recombinant fusion protein, with pH from about 7.2 to about 7.6.

Administration of Recombinant Fusion Proteins

Fusion protein compositions are prepared for administration by mixing fusion protein having the desired degree of purity with physiologically acceptable carders. Such carriers will be nontoxic to recipients at the dosages and concentrations employed. Ordinarily, the preparation of such compositions entails combining the fusion protein with buffers, antioxidants such as ascorbic acid, low molecular weight (less than about ten residues) polypeptides, proteins, amino acids, carbohydrates including glucose, sucrose or dextrins, chelating agents such as EDTA, glutathione and other stabilizers and excipients.

Fusion protein compositions may be used to enhance proliferation, differentiation and functional activation of hematopoietic progenitor cells, such as bone marrow cells. Specifically, compositions containing the fusion protein may be used to increase peripheral blood leukocyte numbers and increase circulating granulocyte counts in myelosuppressed patients. To achieve this result, a therapeutically effective quantity of a fusion protein composition is administered to a mammal, preferably a human, in association with a pharmaceutical carrier or diluent.

The following examples are offered by way of illustration, and not by way of limitation.

EXAMPLE 1

Expression and Purification of GM-CSF/IL-3 Fusion protein from pIXY321

Precultures were started by inoculating flasks of selective medium with S. cerevisiae XV2181 containing the expression plasmid pIXY321. The resultant precultures were grown for approximately 24 hours, then utilized in the large-scale production of recombinant fusion proteins. The culture conditions of the large-scale fermentation (including temperature, agitation, aeration, pH, back pressure and nutrient feed rate) were monitored and maintained within optimal parameters throughout the fermentation. At the end of the fermentation process, the fermenters were cooled to room temperature, and the pH of the yeast fermentation broth was adjusted to 8.0–9.0. The fermentation broth was then clarified to separate the broth from the biomass. The clarified broth was filtered with an absolute 0.2 gm filter, into a sterile tank and held at 2–8° C. until the next purification step.

The clarified broth was concentrated approximately 5 fold, then subjected to constant volume diafiltration using two volumes of purified water. The pH of the diafiltered broth was adjusted to pH 5.0 using glacial acetic acid. The concentrated, diafiltered broth was further purified on a series of ion exchange resins. The concentrated, diafiltered broth was applied to a 35 cm×3.7 cm column (3.6 L) packed with the cation exchange resin SP-Toyopearl™ (approximately 1 ml resin per 60 fermentation broth) equilibrated with 25 mM sodium acetate, pH 4.0. The absorbance of the effluent was monitored at 280 nm. Following application of the concentrated, diafiltered broth, the column was washed to baseline absorbance with 25 mM sodium acetate, pH 5.5. A Millipak 20 filter was attached to the outlet of the column, and the recombinant fusion protein was step-eluted from the SP-Toyopearl™ using 25 mM sodium acetate, pH 5.5, 400 mM NaCl. A single elution pool was collected. When the absorbance began to increase, collection was begun, and continued while the absorbance formed a peak, until absorbance returned to less than 10% of the full peak height. The elution pool (volume of approximately 8 L) was stored at 2–8° C. until the next purification step.

The elution pool from the SP-Toyopearl™ column was diluted five fold using purified water to adjust the conductivity to approximately 9 mS. The pH of the diluted elution pool was adjusted to pH 8.0±0.2 by making the diluted elution pool approximately 10 mM TrisHCl by the addition of 1.0 M TrisHCl, and adjusting with 1M NaOH. The diluted elution pool was then loaded onto a 25 cm×13 cm (6.4 L) DEAE Sepharose® Fast Flow column (approximately 1 ml of resin per 35 ml of fermentation broth) which had been equilibrated with 25 mM TrisHCl, pH 8.0±0.2. The absorbance of the effluent was monitored at 280 nm. The column was washed with at least two column volumes of 25 mM TrisHCl, pH 8.0±0.2, then with 50 mM sodium acetate, pH 5.0±0.2, to baseline absorbance. A Millipak 20 filter was attached to the outlet of the column, and the recombinant fusion protein was step-eluted with 50 mM sodium acetate, pH 4.5±0.2. When the absorbance began to increase, collection was begun, and continued while the absorbance formed a peak, until absorbance returned to less than 10% of the full peak height. The volume of the elution pool was approximately 8.5 L.

The elution pool from the DEAE Sepharose column was made approximately 10 mM with sodium phosphate, and the pH was adjusted to 6.5±0.2 using 50% NaOH. The adjusted elution pool was then loaded onto a 14 cm×12 cm (1.9 L) Bakerbond Wide Pore™ PEI (WP-PEI; approximately 1 ml resin per 110 ml of fermentation broth) column equilibrated with 10 mM sodium phosphate, pH 6.5±0.2. The absorbance of the effluent was monitored at 280 nm. The column was washed with 10 mM sodium phosphate, pH 6.5±0.2 to baseline absorbance. A Millipak 20 filter was attached to the outlet of the column, and the recombinant fusion protein was step-eluted with 400 mM NaCl in 25 mM sodium phosphate, pH 6.5±0.2. When the absorbance began to increase, collection was begun, and continued while the absorbance formed a peak, until absorbance returned to less than 10% of the full peak height. The volume of the WP-PEI elution pool containing the recombinant fusion protein was approximately 2.3 liters.

The WP-PEI elution pool was diluted approximately 5 fold with water, made approximately 25 mM with sodium acetate, and the pH adjusted to 4.0±0.2 using concentrated hydrochloric acid. The material was then loaded onto a 14 cm×17 cm (2.6 L) cation exchange Fractogel® SO$_3$-650 column (approximately 1 ml resin per 80 ml fermentation broth), which had been equilibrated with 25 mM sodium acetate, pH 4.0±0.2. The absorbance of the effluent was monitored at 280 nm. The column was washed with a minimum of two column volumes of 25 mM sodium acetate, pH 4.0±0.2. The column was then washed with 25 mM 4-morpholineethanesulfonic acid (MES), pH 5.5 (Buffer A) until the pH of the buffer and the effluent were within 0.2. A linear gradient of 25 mM MES, pH 5.5, 500 mM NaCl (Buffer B) was established from 100% A to 100% B at a rate of approximately 0.3%/minute, and the column was eluted at a flow rate of 121 ml minute. Five-hundred ml fractions were collected; those fractions containing the purified recombinant fusion protein were pooled to yield a total volume of approximately 11.5 L. The elution pool was concentrated by ultrafiltration to a concentration of at least about 5 mg/ml, and the buffer was exchanged with 0.1 M TrisHCl, pH 7.4. The resultant purified, concentrated fusion protein preparation (purified drug concentrate) was analyzed to determine purity and activity as described in Example 2.

EXAMPLE 2

Analysis of Purified Recombinant Fusion Protein from pIXY321

The purified drug concentrate was a clear colorless liquid containing less than 10 pg of DNA per mg of protein, and less than 10 units of endotoxin per mg of protein by a limulus amoebocyte assay. Samples of the pool containing the purified recombinant fusion protein were diluted in sample buffer (0.1 M Tris, pH 6.8, 2% SDS, 20% glycerol, 0.1 pyronin Y, 0.01% bromphenol blue) with and without reducing agent (2% 2-mercaptoethanol), and applied to the wells of a e 10–20% gradient polyacrylamide gel (stacking gel: 0.12 M Tris, pH 6.8, 4.6% acrylamide, 0.12% bis-acrylamide, 0.1% SDS; running gel: 0.37 M Tris, pH 8.8, 0.1% SDS, 10–20% acrylamide, 0.54–0.26% bisacrylamide). The samples were electrophoresed at 30–40 mA constant current until the tracking dye reached the bottom of the gel. The gel was then placed in 0.2% Coomassie Brilliant Blue R250, 45% methanol, 10% acetic acid to stain for approximately one hour, then destained with 25% methanol, 7.5% acetic acid until the background was clear and the protein bands visible. The reduced SDS-PAGE gels were analyzed by densitometric scanning to assess the relative purity of the purified recombinant fusion protein preparation. Scanning densitometry of the gel stained with Coomassie blue indicated that the protein present in the pool consisted of greater than 98% recombinant fusion protein.

Similar 10–20% gels were prepared, and samples were diluted in sample buffer and electrophoresed in substantially the same manner. The electrophoresed gels were placed in 5% methanol, 7% acetic acid for 30 to 35 minutes, then rinsed twice with purified water and immersed in 2.5% glutaraldehyde for 30 to 35 minutes. Subsequently, the gels were rinsed four times with purified water, and placed in 100 ml of 95% ethanol for 5 to 10 minutes. The 95% ethanol was diluted to 50% with purified water, and the gel was incubated for and additional 10 to 15 minutes. The gel was then transferred to a solution of 10% ethanol for a minimum of 30 minutes, after which it was stained with silver stain solution (0.78% w/v silver nitrate) for twelve to fifteen minutes. The gel was then rinsed with purified water at least five times, and transferred to developing solution (0.5% citric acid, 1.9% formaldehyde, 10% ethanol) and incubated until protein bands were resolved. Development was stopped by placing the gel in 10% acetic acid. By silver stain, there were no proteins other than the recombinant fusion protein present in the recombinant fusion protein preparation.

Proteins resolved by SDS-PAGE were electrophoretically transferred to nitrocellulose, and analyzed by Western blot using monoclonal antibodies to recombinant human GM-CSF and recombinant human IL-3. Following electrophoresis, gels were soaked in transfer buffer (192 mM glycine, 25 mM Tris, 20% methanol), then placed on 3 mm filter paper on transfer cassettes. Nitrocellulose (0.45 gm pore size) that had been soaked in transfer buffer was placed over each gel. The nitrocellulose was overlaid with two pieces of 3 mm filter paper, and the transfer cassettes assembled. The assembled transfer cassettes were place in an electrophoresis chamber containing transfer buffer, oriented in such a way that the nitrocellulose was positioned between the gel and the anode. Transfer of the proteins from the gel to the nitrocellulose was accomplished by electrophoresis at 1 amp for one to two hours. The transfer cassettes were removed form the electrophoresis chamber, and blocked with 3% bovine serum albumen in 50 mM Tris pH 7.5, 150 mM sodium chloride (TBS-3% BSA) for 30 to 35 minutes. The nitrocellulose was then washed twice with phosphate buffered saline (PBS) and incubated with monoclonal antibody to human GM-CSF (5 µg/ml in TBS-3% BSA) for approximately one hour. A duplicate blot was incubated with monoclonal antibody to IL-3 (10 µg/ml in TBS-3% BSA) for approximately one hour. The blots were then washed with PBS, and incubated with goat anti-mouse IgG-peroxidase conjugate diluted 1:200 in TBS-3% BSA for approximately one hour. Following completion of the second incubation step, the blots were washed with PBS and incubated with color development reagent, using 4-chloro naphthol as the substrate for the peroxidase. Both monoclonal antibodies to human GM-CSF and human IL-3 bound to the recombinant fusion protein and gave a positive result by Western blot.

The purity of the recombinant fusion protein was also evaluated by analytical reverse phase-HPLC using a Vydac C18 column (4.6 mm×25 cm, 10 gm, 300 angstrom) equilibrated in 0.1% trifluoroacetic acid (TFA). A gradient of acetonitrile, 0.1% TFA was established at a rate of change of 2% per minute (0 to 80%) to elute the recombinant fusion protein from the column. A peak corresponding to the recombinant fusion protein was detected at a retention time corresponding to that of a reference standard preparation of recombinant fusion protein (a preparation that had been previously purified and been shown to be substantially pure). The results indicated that the recombinant fusion protein formed greater than 99% of the protein present in the purified drug concentrate.

The amino acid composition and amino terminal sequence of the purified recombinant fusion protein were also determined. The amino acid composition was consistent with that of a reference standard of recombinant fusion protein. The amino terminus was also consistent with that of a reference standard recombinant fusion protein. Isoelectric focusing was also performed to determine the isoelectric point of the recombinant fusion protein. The pI bands seen were consistent with those of a reference standard recombinant fusion protein.

The potency of the purified recombinant fusion protein was evaluated in a cell proliferation assay using TF-1 cells. TF-1 cells are a continuous cell line derived from human erythroid leukemia cells, and are dependent on IL-3 or GM-CSF for growth. TF-1 cells were maintained in medium containing GM-CSF. Prior to being used in an assay, the cells were washed free of GM-CSF, and resuspended to a concentration of $5 \times 10^4$ cells/ml in assay medium (Iscove's Modification of Dulbecco's Medium). The suspended cells were added to the wells of a 96-well microtiter plate containing dilutions of the recombinant fusion protein preparation, positive controls, or negative controls. The cells were incubated at 37° C. for 72 hours; proliferation was measured by adding tritiated thymidine for the final four hours of the incubation. The cells were harvested onto glass fiber filters, and the amount of radioactivity incorporated was determined by scintillation counting. The potency of the purified recombinant fusion protein was $2.1 \times 10^8$ U/mg (a unit is defined as the amount of recombinant fusion protein that induces half-maximal proliferation in the TF-1 bioassay).

The binding affinity of the recombinant fusion protein for receptors for both GM-CSF and IL-3 were determined substantially as described by Park et al., J. Biol. Chem. 264:5420; 1989, and Park et al., Blood 74:56; 1989. The binding affinity for GM-CSF receptor was $1.0 \times 10^{10}$ M$^{-1}$; for IL-3 receptor, $2.2 \times 10^{10}$ M$^{-1}$.

EXAMPLE 3

Expression and Purification of IL-3/GM-CSF Fusion Protein from pIXY344

Yeast cells containing the plasmid pIXY344 were cultured to express and secrete IL-3/GM-CSF fusion protein into suitable culture medium. The culture yielded approximately 950 ml of fermentation broth, which was clarified by centrifugation to remove the yeast cells. After centrifugation, the volume of clarified broth was about 720 ml; the broth was furthered clarified by filtration through a 0.45 gm cutoff filter. The clarified broth was concentrated to a volume of approximately 70 ml by tangential flow filtration using 10K MW cutoff membranes. The concentrated broth was diafiltered with about 240 ml water to decrease the ionic strength to 7.6 mS. The diafiltration system was flushed with approximately 50 ml of water to yield approximately 150 ml of concentrated fluid, resulting in an approximate five-fold concentration of the clarified broth. The concentrated broth, which appeared slightly turbid, was stored overnight at 2–8° C.

The following day, the pH of the concentrated broth was adjusted to pH 4.5 with 2N HCl, after which the broth was applied to a 3.2 cm×5.5 cm column packed with SP-Toyopearl™ that had been equilibrated with 25 mM sodium acetate, pH 4.0. The column was washed with approximately 120 ml of 25 mM sodium acetate, pH 5.5, until the pH of the effluent was 5.5. The recombinant fusion protein was eluted with 25 mM sodium acetate, pH 5.5/400 mM sodium chloride, yielding about 60 ml of eluate.

The eluate from the SP-Toyopearl™ column was diluted approximately three-fold with water and made 10 mM TrisHCl, after which the pH was adjusted with 2 M sodium hydroxide. The final pH of the adjusted material was approximately 8.0, and the ionic strength was 9.75 mS. The adjusted material was loaded onto a 3.2×4 cm DEAE Sepharose® Fast Flow column which had been equilibrated with 25 mM TrisHCl, pH 8.0±0.2. The column was washed with 50 mM sodium acetate, pH 5.0±0.2 until the pH of the effluent was 5.0 (approximately 500 ml). The recombinant fusion protein was stepeluted with 50 mM sodium acetate, pH 4.5±0.2, yielding approximately 100 ml of eluate.

The eluate from the DEAE Sepharose column was made 10 mM with sodium phosphate, the pH adjusted to 6.5±0.2 using 2 M sodium hydroxide, and loaded onto a 2.2 cm×1.8 cm Bakerbond Wide Pore™ PEI (polyethyleneimine) column equilibrated with 10 mM sodium phosphate, pH 6.5±0.2. After the recombinant fusion protein bound, the column was washed with 10 mM sodium phosphate, pH 6.5±0.2 followed by a step elution using 400 mM NaCl in 25 mM sodium phosphate, pH 6.5±0.2. The volume of the WP-PEI elution pool containing the recombinant fusion protein was approximately 11 ml. The WP-PEI elution pool was analyzed by SDS-PAGE, and found to contain a homogeneous recombinant fusion protein.

What is claimed is:

1. A method for purifying a recombinant fusion protein comprising ganulocyte-nacrophage colony stimluating factor (GM-CSF) and Interfusion-3(IL-3) from an aqueous solution, consisting essentially of the steps of:

(a) adsorbing the recombinant fusion protein to a cation exchange resin;

(b) eluting the recombinant fusion protein from the cation exchange resin;

(c) adsorbing the recombinant fusion protein from step (b) to a first anion exchange resin;

(d) eluting the recombinant fusion protein from the first anion exchange resin;

(e) adsorbing the recombinant fusion protein from step (d) to a second anion exchange resin; and (f) eluting the recombinant fusion protein from the second anion exchange resin.

2. A method according to claim 1, wherein the cation exchange resin is selected from the group consisting of cellulose-based, agarose-based, dextran-based, silica-based and synthetic polymer-based matrices having functional groups selected from the group consisting of sulfonate, sulfopropyl, and carboxymethyl groups; the first anion exchange resin is selected from the group consisting of cellulose-based, agarose-based, dextran-based, silica-based and synthetic polymer-based matrices having functional groups selected from the group consisting of quaternary amino and diethylaminoethyl groups; and the second anion exchange resin is selected from the group consisting of cellulose-based, agarose-based, dextran-based, silica-based and synthetic polymer-based matrices having functional groups selected from the group consisting of quaternary amino, diethylaminoethyl and polyethyleneimine groups.

3. A method according to claim 2, wherein the cation exchange resin is SP-Toyopearl™, the first anion exchange resin is DEAE Sepharose® Fast Flow, and the second anion exchange resin is Bakerbond Wide Pore™ PEI.

4. A method according to claim 1, further consisting of:

adsorbing the recombinant fusion protein eluted from the second anion exchange resin to a second cation exchange resin; and eluting the recombinant fusion protein from the second cation exchange resin.

5. A method according to claim 4, wherein the second cation exchange resin is selected from the group consisting of cellulose-based, agarose-based, dextran-based, silica-based and synthetic polymer-based matrices having functional groups selected from the group consisting of sulfonate, sulfopropyl and carboxymethyl groups.

6. A method according to claim 5, wherein the second cation exchange resin is Fractogel® SO$_3$-650

7. A method for purifying a recombinant fusion protein comprising granulocyte-nacrophage colony stimulating factor (GM-CSF) and Interleukin-3 (IL-3) from an aqueous solution containing recombinant fusion protein comprising GM-CSF and IL-3, consisting essentially of the steps of:

(a) adsorbing the recombinant fusion protein to a first anion exchange resin;

(b) eluting the recombinant fusion protein from the first anion exchange resin;

(c) adsorbing the recombinant fusion protein from step (b) to a cation exchange resin;

(d) eluting the recombinant fusion protein from the cation exchange resin;

(e) adsorbing the recombinant fusion protein from step (d) to a second anion exchange resin; and (f) eluting the recombinant fusion protein from the second anion exchange resin.

8. A method according to claim 7, wherein the first anion exchange resin is selected from the group consisting of cellulose-based, agarose-based, dextran-based, silica-based and synthetic polymer-based matrices having functional groups; selected from the group consisting of quaternary amino and diethylaminoethyl groups, the cation exchange resin is selected from the group consisting of cellulose-based, agarose-based, dextran-based, silica-based and synthetic polymer-based matrices having functional groups selected from the group consisting of sulfonate, sulfopropyl, and carboxymethyl groups; and the second anion exchange resin is selected from the group consisting of cellulose-based, agarose-based, dextran-based, silica-based and synthetic polymer-based matrices having functional groups selected from the group consisting of quaternary amino, diethylaminoethyl and polyethyleneimine groups.

9. A method according to claim 8, wherein the first anion exchange resin is DEAE Sepharose® Fast Flow, the cation exchange resin is SP-Toyopearl™, and the second anion exchange resin is Bakerbond Wide Pore™ PEI.

10. A method according to claim 7, further consisting of:
   adsorbing the recombinant fusion protein eluted from the second anion exchange resin to a second cation exchange resin; and
   eluting the recombinant fusion protein from the second cation exchange resin.

11. A method according to claim 10, wherein the second cation exchange resin is selected from the group consisting of cellulose-based, agarose-based, dextran-based, silica-based and synthetic polymer-based matrices having functional groups selected from the group consisting of sulfonate, sulfopropyl and carboxymethyl groups.

12. A method according to claim 11, wherein the second cation exchange resin is Fractogel® SO$_3$-650.

13. A method for purifying a recombinant fusion protein comprising granulocyte-nacrophage colony stimulating factor (GM-CSF) and Interleukin-3 (IL-3) consisting essentially of the steps of:
   (a) culturing cells containing a plasmid selected from the group consisting of pIXY321 and pIXY344 to allow expression and secretion of the recombinant fusion protein into an aqueous culture medium;
   (b) clarifying the aqueous culture medium to remove the cultured cells without removing the recombinant fusion protein;
   (c) concentrating the recombinant fusion protein in the aqueous culture medium to yield a volume of fluid convenient for further processing;
   (d) applying the concentrated fluid containing the recombinant fusion protein to a cation exchange resin;
   (e) adsorbing the recombinant fusion protein the to cation exchange resin;
   (f) washing the cation exchange resin to remove contaminating proteins;
   (g) eluting the recombinant fusion protein from the cation exchange resin to form an elution pool containing the recombinant fusion protein;
   (h) applying the elution pool from step (g) to a first anion exchange resin;
   (i) adsorbing the eluted recombinant fusion protein to the first anion exchange resin;
   (j) washing the first anion exchange resin to remove contaminating proteins;
   (k) eluting the recombinant fusion protein from the first anion exchange resin to form an elution pool containing the recombinant fusion protein;
   (l) applying the elution pool from step (k) to a second anion exchange resin;
   (m) adsorbing the recombinant fusion protein to the second anion exchange resin;
   (n) washing the second anion exchange resin to remove contaminating proteins; and
   (o) eluting the recombinant fusion protein from the second anion exchange resin to form an elution pool containing the recombinant fusion protein.

14. A method according to claim 13, wherein the cation exchange resin is selected from the group consisting of cellulose-based, agarose-based, dextran-based, silica-based and synthetic polymer-based matrices having functional groups selected from the group consisting of sulfonate, sulfopropyl, and carboxymethyl groups; the first anion exchange resin is selected from the group consisting of cellulose-based, agarose-based, dextran-based, silica-based and synthetic polymer-based matrices having functional groups selected from the group consisting of quaternary amino and diethylaminoethyl groups; and the second anion exchange resin is selected from the group consisting of cellulose-based, agarose-based, dextran-based, silica-based and synthetic polymer-based matrices having functional groups selected from the group consisting of quaternary amino, diethylaminoethyl and polyethyleneimine groups.

15. A method according to claim 14, wherein the cation exchange resin is SP-Toyopearl™, the first anion exchange resin is DEAE Sepharose® Fast Flow, and the second anion exchange resin is Bakerbond Wide Pore™ PEI.

16. A method according to claim 15, wherein the recombinant fusion protein is eluted from the cation exchange resin by the addition of 25 mM sodium acetate buffer, pH 5.5, 400 mM sodium chloride, from the first anion exchange resin by the addition of 50 mM sodium acetate buffer, pH 4.5, and from the second anion exchange resin PEI by the addition of 25 mM sodium phosphate buffer, pH 5.5, 400 mM sodium chloride.

17. A method according to claim 13, further consisting of:
   (p) applying the aqueous eluate from step (o) to a second cation exchange resin;
   (q) adsorbing the recombinant fusion protein to the second cation exchange resin;
   (r) washing the second cation exchange resin to remove contaminating proteins; and
   (s) eluting the recombinant fusion protein from the second cation exchange resin to form an aqueous eluate containing the recombinant fusion protein.

18. A method according to claim 17, wherein the second cation exchange resin is selected from the group consisting of cellulose-based, agarose-based, dextran-based, silica-based and synthetic polymer-based matrices having functional groups selected from the group consisting of sulfonate, sulfopropyl, and carboxymethyl groups; the first anion exchange resin is selected from the group consisting of cellulose-based, agarose-based, dextran-based, silica-based and synthetic polymer-based matrices having functional groups selected from the group consisting of quaternary amino and diethylaminoethyl groups; and the second anion exchange resin is selected from the group consisting of cellulose-based, agarose-based, dextran-based, silica-based and synthetic polymer-based matrices having functional groups selected from the group consisting of quaternary amino, diethylaminoethyl and polyethyleneimine groups.

19. A method according to claim 18, wherein the second cation exchange resin is Fractogel® $SO_3$-650.

20. A method according to claim 19, wherein the recombinant fusion protein is eluted from the second cation exchange resin by the addition of a sodium chloride gradient from 0 mM sodium chloride, 25 mM 4-morpholineethanesulfonic acid (MES) buffer, pH 5.5 to 500 mM sodium chloride, 25 mM MES buffer, pH 6.0.

* * * * *

UNITED STATES PATENT AND TRADEMARK OFFICE
CERTIFICATE OF CORRECTION

PATENT NO. : 5,463,029
DATED : October 31, 1995
INVENTOR(S) : Joseph T. Dunn and Stephen M. Waugh It is certified that error appears in the above-indentified patent and that said Letters Patent is hereby corrected as shown below:

Column 3, lines 32 and 33, please underline the heading of -- Source of Recombinant Fusion Proteins comprising GM-CSF and IL-3 --.
Column 5, line 7, replace "53 157" with -- 53157 --.
Column 5, line 67, please underline the heading of -- Protein Expression in Recombinant Microbial Systems --.
Column 8, line 39, please underline the heading of -- Purification of Recombinant Fusion Proteins --.
Column 13, line 8, please underline the heading of -- Administration of Recombinant Fusion Proteins --.
Column 13, line 11, replace "carders" with -- carriers --.
Column 13, lines 35 and 36, please underline the heading of -- Expression and Purification of GM-CSF/IL-3 Fusion Protein from PIXY321 --.
Column 15, lines 8 and 9, please underline the heading of -- Analysis of Purified Recombinant Fusion Protein from pIXY321 --.
Column 17, lines 8 and 9, please underline the heading of -- Expression and Purification of IL-3/GM-CSF Fusion Protein from pIXY344 --.
Column 17, line 16, replace "gm" with -- $\mu$m --.
Column 17, line 25, replace "ovemight" with -- overnight --.
Column 17, line 64, replace "comprising ganulocyte-nacrophage" with -- consisting essentially of granulocyte-macrophage --.
Column 17, line 64, replace "stimluating" with -- stimulating --.
Column 18, line 33, please insert -- (g) -- before the word adsorbing.
Column 18, line 36, please insert -- (h) -- before the word eluting.
Column 18, line 48, replace "-nacrophage" with -- -macrophage --.
Column 19, line 18, please insert -- (g) -- before the word adsorbing.
Column 19, line 21, please insert -- (h) -- before the word eluting.

UNITED STATES PATENT AND TRADEMARK OFFICE
CERTIFICATE OF CORRECTION

PATENT NO. : 5,463,029
DATED : October 31, 1995
INVENTOR(S) : Joseph T. Dunn, et al.

It is certified that error appears in the above-indentified patent and that said Letters Patent is hereby corrected as shown below:

Column 19, line 32, replace "-nacrophage" with -- -macarophage --.

Signed and Sealed this

Eighth Day of October, 1996

Attest:

BRUCE LEHMAN

Attesting Officer     Commissioner of Patents and Trademarks